United States Patent [19]
Pettit et al.

[11] Patent Number: 5,521,284
[45] Date of Patent: May 28, 1996

[54] HUMAN CANCER INHIBITORY PENTAPEPTIDE AMIDES AND ESTERS

[75] Inventors: George R. Pettit, Paradise Valley; Jayaram K. Srirangam, Tempe, both of Ariz.

[73] Assignee: Arizona Board of Regents acting on behalf of Arizona State University, Tempe, Ariz.

[21] Appl. No.: 283,806

[22] Filed: Aug. 1, 1994

[51] Int. Cl.$^6$ .......................... A61K 38/00; A61K 38/04; C07K 5/00; C07K 74/00
[52] U.S. Cl. ............................................ 530/330; 530/331
[58] Field of Search ...................................... 530/330, 331

[56] References Cited

U.S. PATENT DOCUMENTS

| | | | |
|---|---|---|---|
| 4,816,444 | 3/1989 | Pettit et al. | 514/17 |
| 5,017,691 | 5/1991 | Lee et al. | 535/351 |

OTHER PUBLICATIONS

Grantham et al, Science vol. 185 p. 862 (1974).
Harper's Review of Biochemistry, 20th ed. p. 17 (1985).
Pettit et al J. Org. Chem vol. 59 p. 2935 (1994).
Hamada et al Tet. Lett. vol. 32 p. 931 (1991).

*Primary Examiner*—Christina Y. Chan
*Assistant Examiner*—A. M. Davenport
*Attorney, Agent, or Firm*—Richard R. Mybeck; Walter R. Mybeck, II; Paula L. Bentley

[57] ABSTRACT

The isolation, elucidation and synthetic replication of novel pentapeptide amides and esters are described. The compounds have the general structure

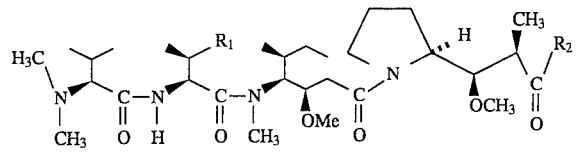

in which $R_1$ and $R_2$ are selected as shown below:

14) $R_1 = -CH_2-CH_3$; $R_2 =$

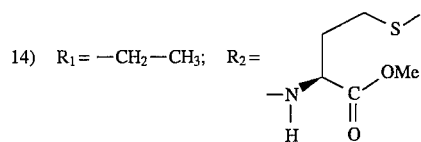

| | |
|---|---|
| $R_1=CH_3$; $R_2=-O-CH_2CH_2CH_2CH_2CH_3$ | 16a) |
| $R_1=CH_3$; $R_2=-O-CH_2CH_2CH_2CH_2CH_2 CH_2CH_2CH_3$ | 16b) |
| $R_1=CH_3$; $R_2=-NH-CH_2CH_2CH_2CH_2CH_2CH_3$ | 16c) |

5 Claims, No Drawings

HUMAN CANCER INHIBITORY PENTAPEPTIDE AMIDES AND ESTERS

INTRODUCTION

Financial assistance for this project was provided by U.S. Government Grant Number OIG-CA-44344-01-05. The United States Government may own certain rights to this invention.

This invention relates generally to the field of cancer chemotherapy and more particularly to the elucidation and synthesis of unique tumor inhibiting peptide amide and ester derivatives of dolastatin 10 which may be useful in chemotherapy.

BACKGROUND OF THE INVENTION

Ancient marine invertebrate species of the Phyla Bryozoa, Molluska, and Porifera have been well established in the oceans for over one billion years. Such organisms have undergone trillions of biosynthetic reactions of their evolutionary chemistry to reach their present level of cellular organization, regulation and defense.

Marine sponges, however, have changed minimally in their physical appearance in the last 500 million years. This suggests that they possess a very effective chemical resistance to evolution in response to changing environmental conditions over that period of time. Recognition of the potential for utilizing this biologically potent marine animal for medicinal purposes was recorded in Egypt about 2,700 B.C. and by 200 B.C. certain sea hare extracts were being used in Greece for their curative affect. This consideration along with the observation that marine animals, e.g. invertebrates and sharks, rarely develop cancer led to the systematic investigation of marine animal and plant species for anticancer compounds.

By 1968, ample evidence had been obtained, based on the U.S. National Cancer Institute's (NCI) key experimental cancer study systems, that certain marine organisms could provide new and antineoplastic and/or cytotoxic agents useful in chemotherapy and might also lead to compounds which would be effective in the control and/or eradication of certain viral diseases.

Further, these marine organisms were believed to possess potentially useful drug candidates of unprecedented structure which had eluded discovery by other methods of medicinal chemistry. Fortunately, these expectations have been realized, e.g. the discovery of the bryostatins, dolastatins and cephalostatins, many of which are now in preclinical development or human clinical studies.

Those researchers presently involved in medicinal chemistry know well the agonizing time lag between the isolation of a new compound and its introduction to the market. Often this procedure takes several years and has been known to take decades. As a result, industry, in association with the U.S. Government, has developed a system of testing criteria which serves two purposes. One is to eliminate those substances which are shown through testing to be economically counterproductive to pursue. The second, and more important purpose is the identification of those compounds which demonstrate a high likelihood of success and therefore merit further study and qualification, and warrant the attendant expense, inevitably necessary to meet the stringent regulatory requirements which control the ultimate market place for such products.

The cost to develop the necessary data required for lawful marketing of a new drug compound currently approaches ten million dollars per compound. Economics dictate that such a huge investment be made only when there is a reasonable likelihood that it can be recouped. Absent such a likelihood, there will be no investment and, without investment, the research requisite for the discovery of these potentially life saving compounds will cease.

Current research in the control of cancer in the United States is coordinated by the National Cancer Institute (NCI). To determine whether a substance has anti-cancer properties, the NCI has established a systematic protocol. This protocol, which involves the testing of a substance against a standard cell line panel containing 60 human tumor cell lines, has been verified and is accepted in scientific circles. The protocol, and the established statistical means for analyzing the results obtained by the standardized testing are fully described in the literature. See: Boyd, Dr. Michael R., *Principles & Practice of Oncology*, PPO Updates, Volume 3, Number 10, October 1989, for an in depth description of the testing protocol; and Paull, K. D., "Display and Analysis of Patterns of Differential Activity of Drugs Against Human Tumor Cell Lines; Development of Mean Graph and COMPARE Algorithm", *Journal of the National Cancer Institute Reports*, Vol. 81, No. 14, Page 1088, Jul. 14, 1989 for a description of the methods of statistical analysis. Both of these references are fully incorporated herein by this reference thereto.

Numerous substances have been discovered which demonstrate significant antineoplastic or tumor inhibiting characteristics. As stated above, many of these compounds have been extracted, albeit with great difficulty, from marine animals such as the sponge and sea hare. Once isolation and testing of these compounds has been accomplished, a practical question remains, namely how to produce commercially significant quantities of the desired substance.

Quinine, which is available in practical quantities from the bark of the cinchona plant, differs from the compounds which are extracts of marine creatures. The collection and processing of these later compounds from their natural sources ranges from grossly impractical to the utterly impossible. Ignoring the ecological impact, the population of these creatures and the cost of collection and extraction make the process unworkable. Elucidation and synthesis of such active compounds is the only practical solution.

Therefore, the elucidation of the structure of these antineoplastic compounds is essential. After the structure has been determined, then a means of synthesis must be determined. This is often a long and arduous procedure due to the idiosyncratic complexity of these naturally occurring, evolutionary modified compounds. In addition, further research is necessary to determine whether any portion of the naturally occurring compound is irrelevant to the desired properties, so that focus can be on the simplest structure having the perceived properties.

The Constitution of the United States (Art. 1, Sec. 8) authorized Congress to establish the United States Patent and Trademark Office (USPTO) to promote scientific progress. In order to obtain patent rights, one must show the utility of the invention. Cancer cell growth in humans often causes pain, suffering, and premature death. The inhibition of human cancerous tumor growth as evidenced by NCI cell line data is utilitarian in that it relieves these conditions, thereby allowing the human thus afflicted to have a longer, more productive life. Little could be more utilitarian than this result.

3

The sole right obtained from the grant of a Letters Patent is to prevent others from exploiting the subject matter of the patent. This grant protects the inventor for a period hopefully adequate to allow the recoupment of the investment in the underlying research. This in turn provides the incentive and the wherewithal for further research.

The recognition of antineoplastic and tumor inhibiting activity as demonstrated by accepted NCI criteria as "utility" can promote research efforts in the United States and is unequivocally essential if those efforts are to obtain even a modest modicum of success. To reject the NCI criteria on any grounds can only result in quashing all further efforts in the United States and leave our people at the mercy of those foreign companies who operate in more foresighted jurisdictions.

BRIEF SUMMARY OF THE INVENTION

The isolation, elucidation and synthetic replication of potentially useful antineoplastic peptides offers one of the most promising approaches to new anticancer drugs. Continuing research towards these objectives has now resulted in the discovery of and synthetic replication of five potent new anticancer peptides. In the syntheses of these peptides, naturally occurring as well as some modified amino acids have been utilized. The modified amino acids chosen here are constituents of the well known dolastatin 10 and dolastatin 15. Both are structurally distinct peptides with excellent antineoplastic activity. Presently, dolastatin 10 represents the most important member of the dolastatin family and is a potentially useful anticancer drug. Herein disclosed are new linear peptides having excellent activity against a series of human cancer cell lines. Structures of the compounds, with their reference numbers, and a synthesis process appear below:

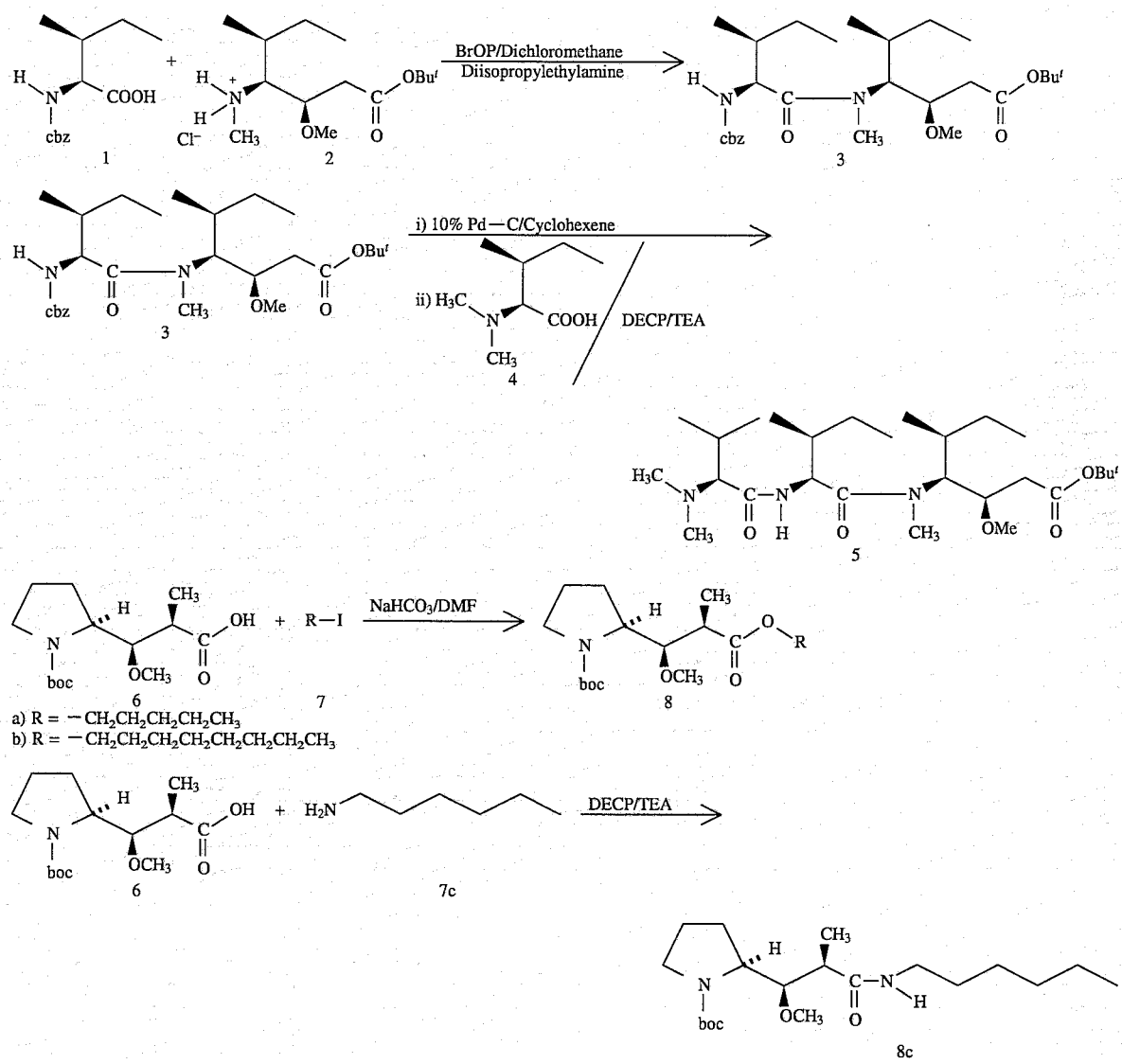

-continued
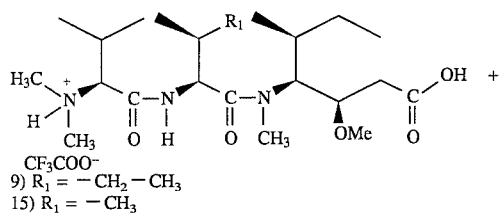
9) $R_1 = -CH_2-CH_3$
15) $R_1 = -CH_3$
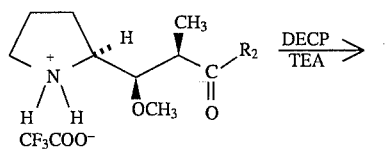
10a) $R_2 = -O-CH_2CH_2CH_2CH_2CH_3$
10b) $R_2 = -O-CH_2CH_2CH_2CH_2CH_2CH_2CH_3$
10c) $R_2 = -NH-CH_2CH_2CH_2CH_2CH_2CH_3$
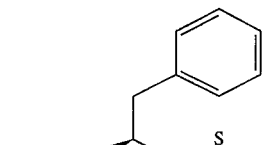
11) $R_2 = $
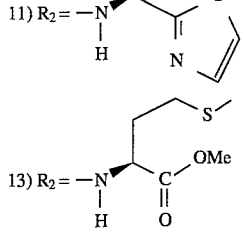
13) $R_2 = $
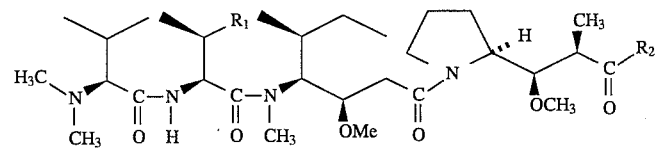
12) $R_1 = -CH_2-CH_3$; $R_2 = $
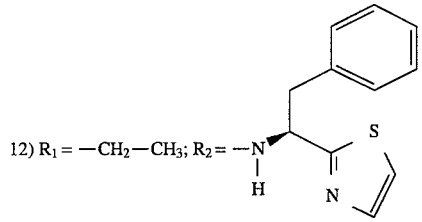
14) $R_1 = -CH_2-CH_3$; $R_2 = $
16a) $R_1 = CH_3$; $R_2 = -O-CH_2CH_2CH_2CH_2CH_3$
16b) $R_1 = CH_3$; $R_2 = -O-CH_2CH_2CH_2CH_2CH_2CH_2CH_3$
16c) $R_1 = CH_3$; $R_2 = -NH-CH_2CH_2CH_2CH_2CH_2CH_3$
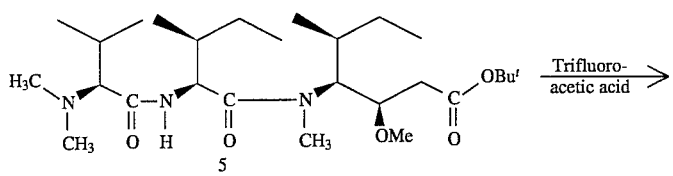

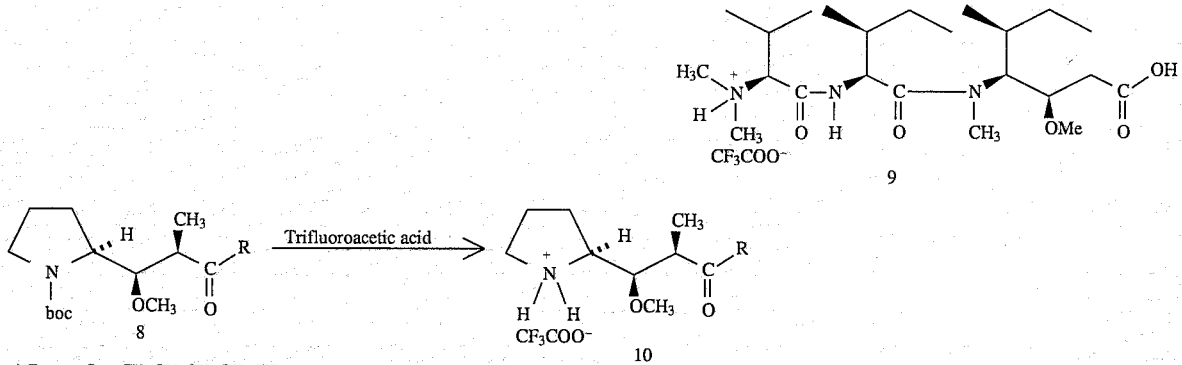

a) R = —O—CH$_2$CH$_2$CH$_2$CH$_2$CH$_3$
b) R = —O—CH$_2$CH$_2$CH$_2$CH$_2$CH$_2$CH$_2$CH$_2$CH$_3$
c) R = —NH—CH$_2$CH$_2$CH$_2$C$_2$CH$_2$CH$_3$

The new peptides disclosed herein were constructed by the introduction of a peptide bond between selected amino acids and modified amino acids and coupling the resulting di- and tri-peptides to obtain novel peptides having very high anticancer activity. (For the ease of the reader, the several compounds will be hereinafter identified by the reference numbers appearing next to them in the flow chart shown above). The present disclosure involves the identification and synthesis of five new compounds, namely, two pentapeptides (12 and 14), two tetrapeptide alkyl esters (16a–b), and a tetrapeptide amide (16c).

The synthesis of these five compounds was achieved, inter alia, using the following procedures:

To achieve the synthesis of the two pentapeptides, 12 and 14, the common peptide 5 is required. Tripeptide 5 was synthesized starting from dolaisoleuine (Dil), a modified amino acid. Dolaisoleuine was coupled with N-cbz-(L)-Isoleucine (1), using BrOP as the coupling agent in the presence of diisopropylethylamine to obtain the dipeptide N-Z-Ile-Dil-OBu$^t$ (3). The N-carbobenzyloxy protecting group of the dipeptide 3 was then removed with 10% Pd-C in cyclohexene to afford the free base which was coupled with dolavaline (Dov, a modified amino acid) using diethylcyanophosphonate as the coupling agent to give the required tripeptide Dov-Ile-Dil-OBu$^t$ (5).

In a similar fashion, three alkyl groups of differing lengths were chosen for the synthesis of the tetrapeptide alkyl esters/amide (16) namely, pentyl, octyl, and hexyl. The required t-boc-Dolaproine esters (8a and 8b) were readily synthesized by the reaction of t-boc-dolaproine (6, a modified amino acid) with the respective alkyl iodides (7a and 7b) in presence of sodium bicarbonate (in dry dimethylformamide). The t-boc Dolaproine amide (8c) was prepared by reaction of t-boc-Dolaproine (6) with hexylamine (7c) λ in prescence of diethylcyanophosphonate and triethylamine. The t-boc protecting groups of the tripeptide (5) as well as the t-boc-dap esters/amide (8a–c) were then removed with trifluoroacetic acid to obtain the respective tfa salts (9, 10a–c).

The resulting tripeptide-tfa salt (9) was coupled with two known dipeptide-tfa salts, namely, 'tfa*Dap-Doe' (11) and 'tfa*Dap-Met-OMe' (13). Both couplings were carried out with DECP resulting in good yields of the 'pentapeptides' (12 and 14). Similarly, the tfa salts of the dap-esters/amide (10a–c) then coupled with the tripeptide-tfa salt, tfa*Dov-Val-Dil-COOH (15) using DECP as the coupling agent to obtain the tetrapeptide esters/amide (16a–c) in good yields.

All these compounds demonstrated excellent growth inhibition when administered to a variety of human cancer and mouse leukemia cell lines. The biological results are disclosed in Tables 1 and 2 below.

Accordingly, the primary object of the subject invention is the identification and synthesis of novel peptide derivatives of dolastatin 10, which demonstrate extraordinary inhibition of cell growth activity.

Another object of the subject invention is to isolate those active portions of dolastatin 10 derivatives which can be attached to other structures to create new compounds which exhibit excellent growth inhibition when measured by a variety of human cancer and mouse leukemia cell lines.

These and still further objects as shall hereinafter appear are readily fulfilled by the present invention in a remarkably unexpected manner as will be readily discerned from the following detailed description of exemplary embodiments thereof.

DESCRIPTION OF THE PREFERRED EMBODIMENT

In vitro testing is an absolutely essential part of the process of discovering new compounds for use in fighting the ravages of cancer. Without screening, the process of obtaining new candidate drugs would be even more complex and expensive. However, to understand this process, and recognize the outstanding results demonstrated by some of the compositions disclosed herein, one must understand the procedures, the nomenclature, and the data analysis involved. A brief description of the appropriate terminology follows:

$ED_{50}$ (P388) and $GI_{50}$ (HTCL) identify the drug dose which reduces the percent tumor/cell growth to 50%. There is no mathematical difference between $ED_{50}$ and $GI_{50}$, both of which are calculated using the same formula. The only difference is historical usage.

TGI, means "Total Growth Inhibition", and identifies the drug dose needed to yield zero percent growth, i.e. there are just as many cells at the end of the experiment as were present at the beginning. Whether just as many cells were killed as were produced (steady state), or no growth occurred (total inhibition) cannot be distinguished.

$LC_{50}$, means "Lethal Concentration 50%", and identifies the drug concentration which reduces to one-half of the cells originally present at the beginning of the experiment.

Each drug is tested at five (5) doses: 100–10–1–0.1–0.01—μg/mL. Percent Growths are calculated for each dose. The two (or three) doses with growth values above, below, (or near to) 50% growth are used to calculate the $ED_{50}/GI_{50}$ values using a linear regression computation. If no dose yields a growth value under 50%, the results are expressed as: $ED_{50}$>(highest dose). If no dose yields growth higher than 50% growth, then $ED_{50}$<(lowest dose). Similar calculations are performed for the TGI at 0% growth, and at −50% growth for the $LC_{50}$.

At the start of each experiment, cells from the in vitro cell cultures are inoculated into the appropriate tubes or microtiter plates. One set of control tubes/plates is immediately counted to determine the number of cells at the start of the experiment. This is the "baseline count", or "Tzero reading". At the end of the experiment (48 hrs later), a second set of control tubes/plates is analyzed to determine the "Control Growth" value. The growth (or death) of cells relative to the initial quantity of cells is used to define the "Percent of Growth."

|  | EXAMPLE: Baseline Count 20 Control Count 200 (10-Fold Growth) |
| --- | --- |
| 100% Growth = Control Growth | 100% Growth = 200 |
| 50% Growth = Tzero + $\frac{\text{Control} - \text{Tzero}}{2}$ | 50% Growth = 110 |
| 0% Growth = Tzero | 0% Growth = 20 |
| −50% Growth = Tzero/2 | −50% Growth = 10 |

Now that the relevant definitions and data analysis techniques have been disclosed, this disclosure can now turn to the particular compounds disclosed herein.

The synthesis of potentially useful peptides presents one of the most essential and promising sources for new types of anticancer and immunosuppressant drugs. The Dolastatins, an unprecedented series of linear and cyclic antineoplastic and/or cytostatic peptides isolated from Indian Ocean sea hare *Dolabella auricularia* represent excellent leads for synthetic modification. The very productive sea hare *Dolabella auricularia* has produced a number of structurally distinct peptides with excellent antineoplastic activity. Presently Dolastatin 10, a linear pentapeptide, represents the most important member and is a potentially useful antineoplastic agent. Dolastatin 10 shows one of the best antineoplastic activity profiles against various cancer screens presently known. Recently the total synthesis and absolute configuration of this structurally unique and biologically active peptide was discovered. This compound has been tested in vivo and demonstrated significant activity, as shown below.

Experimental Anticancer Activity of Dolastatin 10 in Murine in vivo Systems, T/C (μg/kg)

| P388 Lymphocytic Leukemia | B16 Melanoma |
| --- | --- |
|  | 238 and 40% cures (11.11) |
|  | 182 (6.67) |
| toxic (13.0) | 205 (4.0) |
| and 17% cures (6.5) | 171 (3.4) |
| and 17% cures (3.25) | 142 (1.44) |
| 137 (1.63) | M5076 Ovary Sarcoma |
| L1210 Lymphocytic Leukemia | toxic (26) |
|  | 166 (13) |
| 152 (13) | 142 (6.5) |
| 135 (6.5) | 151 (3.25) |
| 139 (3.25) | LOX Human Melanoma Xenograph (Nude Mouse) |
| 120 (1.63) |  |
|  | toxic (52) |
|  | 301 and 67% cures (26) |
|  | 301 and 50% cures (13) |
|  | 206 and 33% cures (6.5) |
|  | 170 and 17% cures (3.25) |
|  | Lox in separate experiments |
|  | 340 and 50% cures (43) |
|  | 181 and 33% cures (26) |
|  | 192 (15) |
|  | 138 and 17% cures (9.0) |
|  | Human Mammary Xenograph Nude Mouse |
|  | Toxic (26) |
|  | 137 (13) |
|  | 178 (6.25) |
|  | OVCAR-3 Human Ovary Xenograph Nude Mouse |
|  | 300 (40) |
| MX-1 Human Mammary Xenograft (Tumor Regression) |  |
| 14 (52) |  |
| 50 (26) |  |
| 61 (13) |  |
| 69 (6.25) |  |

T/C = Test Control, both bearing tumor, expressed in time of survival.
T/C − 100 = % life extension.

Dolastatin 10 has also been tested against a minipanel from the NCI Primary screen. These results appear below, showing the amount of Dolastatin 10 required to attain $GI_{50}$ in μg/ml, against the cell lines set forth below.

$$\frac{OVCAR\text{-}3}{9.5 \times 10^{-7}} \text{ (A)} \quad \frac{SF\ 295}{7.6 \times 10^{-8}} \text{ (B)} \quad \frac{A498}{2.6 \times 10^{-5}} \text{ (C)}$$

$$\frac{NCI\text{-}H460}{3.4 \times 10^{-6}} \text{ (D)} \quad \frac{KM20L2}{4.7 \times 10^{-6}} \text{ (E)} \quad \frac{SK\text{-}MEL\text{-}5}{7.4 \times 10^{-6}} \text{ (F)}$$

Similarly, compounds 12, 14, 16a, 16b and 16c of the present invention have also been tested against an NCI in vitro mini panel. For each of six cell lines, $GI_{50}$, TGI, and $LC_{50}$ amounts were also calculated for each of the compounds. Each compound was also tested against the PS-388 cell line and for this test an $ED_{50}$ was calculated.

The protocols followed, for the NCI minipanel are, except for the number of cell lines, those established by M. R. Boyd Ph.D., and well known to those of ordinary skill in the art. The procedure followed for the test against PS-388 Leukemia is the same that was followed in the superseded NCI P-388 screening test, which is also well known to those having ordinary skill in the art.

TABLE 1

The Human Cancer Cell-line and P-388 mouse-Leukemia data for the compounds 12 and 14.

|  | Cell type | Cell line | 12 | 14 |
|---|---|---|---|---|
| GI-50 (μg/ml) | Ovarian | OVCAR-3 | 0.0000000091 | 0.000067 |
|  | CNS | SF-295 | 0.000000025 | 0.00025 |
|  | Renal | A498 | 0.000000058 | 0.00027 |
|  | Lung-NSC | NCI-H460 | 0.0000000058 | 0.00012 |
|  | Colon | KM20L2 | 0.0000000072 | 0.000034 |
|  | Melanoma | SK-MEL-5 | 0.0000000048 | 0.000044 |
| TGI (μg/ml) | Ovarian | OVCAR-3 | 0.000000060 | 0.00067 |
|  | CNS | SF-295 | 0.00000025 | >1 |
|  | Renal | A498 | 0.017 | 0.035 |
|  | Lung-NSC | NCI-H460 | 0.000000065 | 0.00013 |
|  | Colon | KM20L2 | 0.0000001 | 0.0013 |
|  | Melanoma | SK-MEL-5 | 0.00000015 | 0.022 |
| LC-50 (μg/ml) | Ovarian | OVCAR-3 | >1 | >1 |
|  | CNS | SF-295 | >1 | >1 |
|  | Renal | A498 | >1 | >1 |
|  | Lung-NSC | NCI-H460 | >1 | >1 |
|  | Colon | KM20L2 | >1 | >1 |
|  | Melanoma | SK-MEL-5 | >1 | >1 |
| ED-50 (μg/ml) | Mouse Leukemia | PS-388 | 0.0000248 | 0.00032 |

TABLE 2

The Human Cancer Cell-line and P-388 Mouse-Leukemia data for the compounds 16a–c.

|  | Cell type | Cell line | 16a | 16b | 16c |
|---|---|---|---|---|---|
| GI-50 (μg/ml) | Ovarian | OVCAR-3 | 0.00052 | 0.0031 | 0.0005 |
|  | CNS | SF-295 | 0.00033 | 0.0054 | 0.0011 |
|  | Renal | A498 | <0.0001 | 0.025 | 0.0019 |
|  | Lung-NSC | NCI-H460 | 0.00034 | 0.0042 | 0.00071 |
|  | Colon | KM20L2 | 0.00033 | 0.0017 | 0.00092 |
|  | Melanoma | SK-NW-5 | 0.00066 | 0.0027 | 0.00058 |
| TGI (μg/ml) | Ovarian | OVCAR-3 | 0.0011 | 0.04 | 0.0039 |
|  | CNS | SF-295 | 0.021 | >1 | >0.01 |
|  | Renal | A498 | 0.18 | 0.55 | >0.01 |
|  | Lung-NSC | NCI-H460 | 0.0011 | 0.058 | 0.0051 |
|  | Colon | KM20L2 | 0.013 | 0.13 | 0.0066 |
|  | Melanoma | SK-NW-5 | 0.031 | >1 | >0.01 |
| LC-50 (μg/ml) | Ovarian | OVCAR-3 | >1 | >1 | >0.01 |
|  | CNS | SF-295 | >1 | >1 | >0.01 |
|  | Renal | A498 | >1 | >1 | >0.01 |
|  | Lung-NSC | NCI-H460 | >1 | >1 | >0.01 |
|  | Colon | KM20L2 | >1 | >1 | >0.01 |
|  | Melanoma | SK-NM-5 | >1 | >1 | >0.01 |
| ED-50 (μg/ml) | Mouse Leukemia | PS-388 | 0.021 | 0.029 | 0.00227 |

In the process of synthesizing the compounds disclosed in this application, certain general procedures are followed. These general procedures are as set forth below.

General Procedure A

The synthesis of N-Z-Ile-Dil-OBu$^t$ (3) was accomplished as follows: To a solution of the hydrochloride salt of Dolaisoleuine t-butyl ester (2, 1 mM) and N-Z-(L)-Isoleucine (1, 1.1 mM) in dry dichloromethane (10 mL), cooled to ice-bath temperature (0°–5° C.) was added diisopropylethylamine (3 mM) followed by BrOP (2 mM) and the resulting solution was stirred at the same temperature for 2 hours. The solvents were removed under reduced pressure and the residue was chromatographed on a silica gel column using 1:3 acetone-hexane as the solvent to obtain the required dipeptide as an oily substance (3, 40%); $R_f$ 0.34 (1:4 acetone-hexane);$[\alpha]_D^{25}$ –7.5° (c 1.19, CHCl$_3$); IR(neat): 3393, 3374, 3295, 2967, 2934, 2878, 1724, 1638, 1528, 1501, 1456, 1412, 1383, 1368, 1296, 1250, 1229, 1153, 1099, 1038, 1028, 980, 959, 845, 777, 739, 698 and 619 cm$^{-1}$; $^1$H NMR(CDCl$_3$, 300 MHz): 7.25(m, 5H, ArH), 5.37 (d, J=9.5 Hz, 1H, NH), 4.99(s, 2H, ArCH$_2$), 4.60(m, 1H, dil N—CH), 4.43(dd, J=6.8 and 9.5 Hz, 1H, Ile C$^\alpha$ H) , 3.79(m, 1H, C<u>H</u>—OMe), 3.24 (s, 3 H, OMe), 2.34(brd, J=15.5 Hz, 1H, HC<u>H</u>—CO), 2.20(dd, J=9.3 and 15.5 Hz, 1H, <u>H</u>CH—CO), 1.50–0.9(m, 6H, 2×CH$_2$, 2×CH), 1.35(s, 9H, t-Bu), 0.88(d, J=8.1 Hz, 3H, CH—C<u>H</u>$_3$), 0.86(d, J=7.2 Hz, 3H, CH—C<u>H</u>$_3$), 0.78(t, J=7.4 Hz, 3H, CH$_2$—C<u>H</u>$_3$) and 0.73(t, J=7.6 Hz, 3H, CH$_2$—C<u>H</u>$_3$); EIMS (m/z): 506(M$^+$, 0.1), 433(0.8), 393(0.7), 347(12), 279(2), 276(3), 248(1), 239(2), 236(1), 230(1), 220(6), 190(4), 186(6), 177(3), 176(18), 172(3), 171(1), 155(2), 154(6), 146(9), 143(3), 141(1), 130(1), 128(4), 108(4), 107(4), 103(6), 101(10), 100(100), 99(2), 98(2), 97(1), 96(1), 95(1), 92(9), 91(78) and 57(18%).

General Procedure B

The synthesis of Dov-Ile-Dil-OBu$^t$ (5) was accomplished as follows: A solution of Z-Ile-Dil-OBu$^t$ (3, 0.2 mM) was dissolved in anhydrous methanol (2 mL) and cyclohexene (2 mL) was added in an argon atmosphere. To the solution was added 10% Pd-C (0.05g) and the mixture was heated at reflux for 10-15 minutes. The catalyst was removed by filtering through a layer of celite, the solvent removed under reduced pressure, and the residue dried in high vacuum for 2 hours.

To a solution of the above free base and N,N-dimethyl-(L)-valine (4, 0.2 mM) in dry dichloromethane (2 mL) was added triethylamine (0.8 mM) followed by DECP (0.22 mM) at 0°-5 °C. under argon atmosphere. After stirring at the same temperature for 2 hours, the solvent was removed and the residue chromatographed on a silica gel column with 1:3 acetone-hexane as solvent to give the required tripeptide t-butyl ester as a colorless solid(5, 65%); m.p. 64°-65 °C.; $R_f$ 0.27(1:4 Acetone-Hexane); $[\alpha]_D^{25}$ –40° (c 0.12, CHCl$_3$); IR(thin film): 3302, 2967, 2934, 2878, 1732, 1661, 1622, 1526, 1485, 1462, 1454, 1416, 1383, 1368, 1300, 1283, 1258, 1200, 1153, 1101, 1037 and 619 cm$^{-1}$; $^1$H NMR(CDCl$_3$, 300 MHz): 6.78(d, J=8.7 Hz, 1H, NH), 4.79(dd, J=7.2 and 9.3 Hz, 1H, Ile C$^a$—H), 4.7(m, 1H, dil CHN), 3.86(m, 1H, CH—OMe), 3.33(s, 3H, OMe), 2.99(s, 3H, dil N—Me), 2.2-2.5(m, 2H, CH$_2$—CO), 2.21(s, 6H, NMe$_2$), 2.05(m, 1H, dov C$^a$—H), 1.2-1.8(m, 7H, 2×CH$_2$, 3×CH), 1.43, 1.54(s, 9H, t-Bu) and 0.75-0.99(m, 18H, 6×CH$_3$); EIMS (m/z): 499(M$^+$, 0.3), 456(0.6), 241(3), 186(1), 128(1), 125(1), 103(2), 101(10), 100 (100), 99(1), 98(1), 91(2), 86(2), 85(3), 84(2), and 57(8%).

General Procedure C

The synthesis of t-Boc-dolaproine esters/amides was accomplished as follows: to a solution of t-Boc-dolaproine (6, 1 mM) in dry dimethylformamide (5 mL) was added the alkyl iodide (7, 1.2 mM) and sodium bicarbonate (2 mM) and the resulting solution was stirred at room temperature for 24 hours. Dichloromethane (50 mL) was added and the organic phase was with water (2×25 mL) and dried. Removal of the solvent in vacuo left behind a residue which was chromatographed on a silica gel column with suitable solvent systems to obtain the required esters.

General Procedure D

To a solution of t-Boc-dolaproine (6, 1 mM) and the amine (7c) in dry dichloromethane (5 mL), cooled to ice-bath temperature under argon atmosphere, was added triethylamine (2 mM) and diethylcyanophosphonate (1.1 mM). The resulting solution was stirred at the same temperature for 1.5 hours. Removal of the solvent in vacuo left a residue which was chromatographed on a silica gel column with suitable solvent system to obtain the required amide.

The t-Boc-Dap Pentyl ester (8a) is prepared by reacting t-Boc-dolaproine (6) with pentyl iodide (7a) following the General Procedure C which gave a residue which was purified on a silica gel column with 1:3 acetone-hexane as the eluent to obtain the required octyl ester as a colorless liquid (8a, 50%); $R_f$ 0.52(1:4 acetone-hexane); $[\alpha]_D^{25}$ –46.8° (c 0.37, CHCl$_3$); IR(neat): 2959, 2932, 2876, 1734, 1697, 1460, 1397, 1366, 1341, 1283, 1258, 1167, 1136, 1098 and 772 cm$^{-1}$; $^1$H NMR(CDCl$_3$, 300 MHz): 3.5-4.1 (m, 4H, N—CH, CH—OMe, OCH$_2$), 3.40(s, 3H, OMe), 3.2(m, 2H, N—CH$_2$), 2.45(m, 1H, CH—CO), 1.55-2.0(m, 4H, 2×dap CH$_2$), 1.46, 1.56(s, 9H, t-Bu), 1.32(m, 6H, 3×CH$_2$), 1.21(d, J=6.8 Hz, 3H, CH$_3$) and 0.88(t, J=6.9 Hz, 3H, CH$_2$—CH$_3$); EIMS (m/z): 325(M$^+$-MeOH, 4), 284(1), 225(1), 171(3), 170(27), 169(2), 168(1), 158(1), 154(1), 138(5), 136(1), 126(1), 118(1), 117(10), 115(7), 114(95), 113(1), 110(4), 103(2), 86 (2), 85(4), 83(1), 82(3), 70(100) and 57(66%).

The t-Boc-Dap Octyl ester (8b) is prepared by reacting t-Boc-dolaproine (6) with octyl iodide (7b) following General Procedure C which gave a residue which was purified on a silica gel column with 1:3 acetone-hexane as the eluent to obtain the required octyl ester as a colorless liquid (8b, 63%); $R_f$ 0.56(1:4 acetone-hexane); $[\alpha]_D^{25}$ –39.5° (c 0.76, CHCl$_3$); IR(neat): 2957, 2930, 2874, 2859, 1734, 1698, 1458, 1395, 1366, 1341, 1256, 1167, 1136, 1099 and 772 cm$^{-1}$; $^1$H NMR(CDCl$_3$, 300 MHz): 3.5-4.1 (m, 4H, N—CH, CH—OMe, OCH$_2$), 3.40(s, 3H, OMe), 3.21(m, 2H, N—CH$_2$), 2.45(m, 1H, CH—CO), 1.55-2.0(m, 4H, 2×dap CH$_2$), 1.46, 1.60(s, 9H, t-Bu), 1.24(m, 15H, 6×CH$_2$, CH—CH$_3$) and 0.85(t, J=6.9 Hz, 3H, CH$_2$—CH$_3$); EIMS (m/z): 367(M$^+$-MeOH, 4), 326(2), 298(1), 267(2), 170(33), 169(2), 158(2), 154(2), 138(5), 136(1), 126(2), 118(1), 117(8), 116(10), 115(8), 114(100), 113(2), 103(2), 86(2), 85(4), 83(2), 82(3), 70(78) and 57(56%).

The t-Boc-Dap-hexylamide (8c) is prepared by reacting t-Boc-dolaproine (6) with hexylamine (7c) following General Procedure D which gave a residue which was purified on a silica gel column with 1:4 acetone-hexane as the eluent to obtain the required hexyl amide as a colorless liquid (8c, 90%); $R_f$ 0.25(1:4 Acetone-Hexane); $[\alpha]_D^{25}$ –47.1° (C 0.21, CHCl$_3$); IR(neat): 3308, 2965, 2932, 2874, 1695, 1670, 1649, 1549, 1456, 1400, 1366, 1286, 1256, 1227, 1171, 1105, 1063, 668, 773 and 725 cm$^{-1}$; $^1$H NMR(CDCl$_3$, 300 MHz): 6.26, 5.65(brs, 1H, NH), 3.3-3.9(m, 2H, N—CH, CH—OMe), 3.41(s, 3H, OMe), 3.20(m, 4H, 2×N—CH$_2$), 2.35 (m, 1H, CH—CO), 1.55-2.0 (m, 4H, 2×dap CH$_2$), 1.46, 1.61(s, 9H, t-Bu), 1.26(m, 11H, 4×CH$_2$, CH—CH$_3$) and 0.85(t, J=7.0 Hz, 3H, CH$_2$—CH$_3$); EIMS (m/z): 338(M$^+$-MeOH), 297, 269, 238, 210, 201, 186, 170, 154, 138, 114, 111, 91, 70(100%) and 57.

General Procedure E

The synthesis of the tripeptide trifluoroacetate salt (9) was accomplished as follows: To a solution of the tripeptide t-butyl ester (5, 0.1 mM) in dichloromethane (2 mL) cooled to ice-bath temperature was added trifluoroacetic acid (2 mL) under argon atmosphere and the solution was stirred at the same temperature for 1 hour. The solvents were then removed under reduced pressure, the residue was dissolved in toluene and solvent again removed under reduced pressure. The residue was dried in vacuo to obtain the tripeptide trifluoroacetate salt(10) as a light yellow sticky mass.

General Procedure F

The synthesis of the DAP ester/amide trifluoroacetate salts (10a-c) was accomplished as follows: To a solution of t-Boc-Dap ester/amide (8a-c, 0.1mM) in dichloromethane (2 mL) cooled to ice-bath temperature was added trifluoroacetic acid (2 mL) under an argon atmosphere and the solution was stirred at the same temperature for 1 hour. The solvents were removed under reduced pressure, the residue was dissolved in toluene and solvent again removed under reduced pressure. The residue was dried in vacuo to obtain a light yellow sticky mass of the respective Dap ester/amide trifluoroacetate salts (10a-c).

General Procedure G

The synthesis of the tetrapeptide esters/amides (12, 14, 16a–c) were accomplished as follows: to a solution of dipeptide or Dap-ester/amide tfa salt (11, 13, 10a–c, 0.1mM) and the tripeptide tfa salt (9, 15, 0.1 mM) in dry dichloromethane (2 mL), cooled to ice-bath temperature (0–5 C) was added triethylamine (4 mM) followed by diethyl cyanophosphonate (1.1 mM). The solution was stirred at the same temperature for 1–2 hours. The solvent was removed under reduced pressure and the residue chromatographed on a silica gel column using the solvents noted below to obtain the respective pentapeptides or tetrapeptide esters/amide (12, 14,& 16a–c).

Compound 12 was synthesized as follows: Coupling of the dipeptide tfa salt (11) with the tripeptide tfa salt (9) following the General Procedure G which gave, following purification on a silica gel column with acetone-hexane (3:2) as the eluent, the required pentapeptide as a colorless solid (12, 55%); m.p. 103°–107 ° C.; $R_f$ 0.55 (acetone-hexane 3:2); $[\alpha]_D^{25}$–67.5° (c 0.08, CHCl$_3$); IR(thin film): 3295, 2965, 2934, 2878, 1620, 1535, 1499, 1452, 1418, 1381, 1202, 1136 and 1099 cm$^{-1}$; EIMS (m/z): 798(M$^+$, 2), 756(2), 755(4), 707(1), 496(1), 495(5), 459(1), 458 (2), 303(1), 242(1), 241(80, 231(1), 214(1), 213(3), 205(1), 198(1), 189(1), 188(10), 187(1), 186(10), 170(4), 169(2), 168(2), 155(1), 154(6), 140(2), 138(3), 128(4), 114(1), 113(3), 112(2), 110(1), 102(26) and 101(100%).

Compound 14 was synthesized as follows: Coupling of the dipeptide tfa salt (13 ) with the tripeptide tfa salt ( 9 ) following the General Procedure G which gave after purification on a silica gel column with acetone-hexane (3:2) as the eluent the required pentapeptide as a colorless thick liquid (14, 86% ); $R_f$ 0.55 (acetone-hexane 3:2); $[\alpha]_D^{25}$–45° (c 0.06, CHCl$_3$); IR(thin film): 3314, 3300, 2967, 2934, 1744, 1640, 1628, 1545, 1441, 1414, 1381, 1277, 1202, 1167, 1098 and 984 cm$^{-1}$; EIMS (m/z): 757(M$^+$, 1), 715(2), 714(6), 496(1), 495(5), 417(1), 241(4), 213 (1), 186(4), 170(2), 154(2), 138(1), 128(2), 127(2), 102(10) and 101 (100%).

Compound Dov-Val-Dil-DaP Pentyl ester (16a) was synthesized as follows: Coupling of the Dap pentyl ester tfa salt (10a) with the tripeptide tfa salt (15) following the General Procedure G and purification using chromatography on a silica gel column with hexane-acetone (3:2) as eluent gave the required tetrapeptide ester as a colorless thick liquid (16a, 30%); $R_f$ 0.39 (hexane-acetone 3:2); $[\alpha]_D^{25}$–69.1° (c 0.23, CHCl$_3$); IR(thin film): 3312, 3295, 2961, 2934, 2876, 1728, 1640, 1452 , 1412, 1389, 1262, 1200, 1169, 1132, 1098 and 1038 cm$^{-1}$; EIMS (m/z): 668(M$^+$, 1), 625(2), 482(3), 227(3), 154(2), 128(2), 102(9) and 101(100%).

Compound Dov-Val-Dil-Dap Octyl ester (16b) was synthesized as follows: Coupling of the Dap pentyl ester tfa salt (10b) with the tripeptide tfa salt (15) following the General Procedure G and purification using chromatography on a silica gel column with hexane-acetone (1:1) as eluent gave the required tetrapeptide ester as a colorless thick liquid (16b, 99%); $R_f$ 0.23 (hexane-acetone 3:1); $[\alpha]_D^{25}$–51.3° (c 0.08, CHCl$_3$); IR(thin film): 3295, 2961, 2932, 2876, 2834, 1730, 1643, 1622, 1526, 1454, 1416, 1385, 1343, 1304, 1262, 1200, 1173, 1134, 1099, 1038 and 721 cm$^{-1}$; EIMS (m/z): 710(M$^+$, 0.7), 667(2), 481(3), 227(4), 199(1), 186 (4), 184(0.9), 155(1), 154(2), 128(2), 117(1), 102(10) and 101(100%).

Compound Dov-Val-Dil-Dap hexylamide (16c) was synthesized as follows: Coupling of the Dap-Hexylamide tfa salt (10c) with the tripeptide tfa salt (15) following the General Procedure G and purification using chromatography on a silica gel column with hexane-acetone (3:2) as eluent gave the required tetrapeptide amide as a colorless thick liquid (16c, 65%); $R_f$ 0.23 (hexane-acetone 3:2); $[\alpha]_D^{25}$–48.8° (c 0.5, CHCl$_3$); IR(thin film): 3308, 3295, 2961, 2930, 2876, 1620, 1545, 1535, 1452, 1416, 1383, 1200, 1167, 1134 and 1099 cm$^{-1}$; EIMS (m/z): 681(M$^+$), 666, 650, 638, 525, 481, 449, 412, 355, 341, 269, 253, 227, 214, 199, 186, 170, 154, 128, 114, 102 and 101(100%).

To further aid in the understanding of the present invention, and not by way of limitation the following examples are presented.

EXAMPLE III-a t-Boc-Dap Pentyl ester (8a)

Reaction of t-Boc-dolaproine (6) with pentyl iodide (7a) following the General Procedure C which gave a residue which was purified on a silica gel column with 1:3 acetone-hexane as the eluent to obtain the required octyl ester as a colorless liquid (8a, 50%); $R_f$ 0.52(1:4 acetone-hexane); $[\alpha]_D^{25}$–46.8° (c 0.37, CHCl$_3$); IR(neat): 2959, 2932, 2876, 1734, 1697, 1460, 1397, 1366, 1341, 1283, 1258, 1167, 1136, 1098 and 772 cm$^{-1}$; $^1$H NMR(CDCl$_3$, 300 MHz): 3.5–4.1 (m, 4H, N—CH, C$\underline{H}$—OMe, OCH$_2$), 3.40 (s, 3H, OMe), 3.2 (m, 2H, N—CH$_2$), 2.45 (m, 1H, CH—CO), 1.55–2.0 (m, 4H, 2×dap CH$_2$), 1.46, 1.56(s, 9H, t-Bu), 1.32(m, 6H, 3×CH$_2$), 1.21(d, J=6.8 Hz, 3H, CH$_3$) and 0.88(t, J=6.9 Hz, 3H, CH$_2$—C$\underline{H}_3$); EIMS (m/z): 325 (M$^+$-MeOH, 4), 284(1), 225(1), 171(3), 170(27), 169(2), 168(1), 158 (1), 154(1), 138(5), 136(1), 126(1), 118(1), 117(10), 115(7), 114 (95), 113(1), 110(4), 103(2), 86(2), 85(4), 83(1), 82(3), 70(100) and 57(66%).

EXAMPLE III-b t-Boc-Dap Octyl ester (8b)

Reaction of t-Boc-dolaproine (6) with octyl iodide (7b) following General Procedure C which gave a residue which was purified on a silica gel column with 1:3 acetone-hexane as the eluent to obtain the required octyl ester as a colorless liquid (8b, 63%); $R_f$ 0.56(1:4 acetone-hexane); $[\alpha]_D^{25}$–39.5° (c 0.76, CHCl$_3$); IR(neat): 2957, 2930, 2874, 2859, 1734, 1698, 1458, 1395, 1366, 1341, 1256, 1167, 1136, 1099 and 772 cm$^{-1}$; $^1$H NMR(CDCl$_3$, 300 MHz): 3.5–4.1(m, 4H, N—CH, C$\underline{H}$—OMe, OCH$_2$), 3.40(s, 3H, OMe), 3.21(m, 2H, N—CH$_2$), 2.45(m, 1H, CH—CO), 1.55–2.0(m, 4H, 2×dap CH$_2$), 1.46, 1.60(s, 9H, t-Bu), 1.24(m, 15H, 6×CH$_2$, CH—C$\underline{H}_3$) and 0.85(t, J=6.9 Hz, 3H, CH$_2$—C$\underline{H}_3$); EIMS (m/z): 367 (M$^+$-MeOH, 4), 326 (2), 298(1), 267(2), 170(33), 169(2), 158(2), 154(2), 138(5), 136 (1), 126(2), 118(1), 117(8), 116(10), 115(8), 114(100), 113(2), 103 (2), 86(2), 85(4), 83(2), 82(3), 70(78) and 57(56%).

EXAMPLE III-c t-Boc-Dap-hexylamide (8c)

Reaction of t-Boc-dolaproine (6) with hexylamine (7c) following General Procedure D which gave a residue which was purified on a silica gel column with 1:4 acetone-hexane as the eluent to obtain the required hexyl amide as a colorless liquid (8c, 90%); $R_f$ 0.25(1:4 Acetone-Hexane); $[\alpha]_D^{25}$–47.1° (c 0.21, CHCl$_3$); IR(neat): 3308, 2965, 2932, 2874, 1695, 1670, 1649, 1549, 1456, 1400, 1366, 1286, 1256, 1227, 1171, 1105, 1063, 668, 773 and 725 cm$^{-1}$; $^1$H NMR(CDCl$_3$, 300 MHz): 6.26, 5.65(brs, 1H, NH), 3.3–3.9(m, 2H, N—CH, C$\underline{H}$—OMe), 3.41(s, 3H, OMe), 3.20(m, 4H, 2×N—CH$_2$), 2.35(m, 1H, CH—CO), 1.55–2.0(m, 4H, 2×dap CH$_2$), 1.46, 1.61(s, 9H, t-Bu), 1.26(m, 11H, 4×CH$_2$, CH—C$\underline{H}_3$) and 0.85(t, J=7.0 Hz, 3H, CH$_2$—C$\underline{H}_3$); EIMS (m/z): 338(M$^+$-MeOH), 297, 269, 238, 210, 201, 186, 170, 154, 138, 114, 111, 91, 70(100%) and 57.

EXAMPLE VI

Dov-Ie-Dil-Dap-Doe (12)

Coupling of the dipeptide tfa salt (11) with the tripeptide tfa salt (9) following the General Procedure G which gave, following purification on a silica gel column with acetone-hexane (3:2) as the eluent, the required pentapeptide as a colorless solid (12, 55%); m.p. 103°–107° C.; R$_f$ 0.55 (acetone-hexane 3:2); [α]$_D^{25}$–67.5° (c 0.08, CHCl$_3$); IR(thin film): 3295, 2965, 2934, 2878, 1620, 1535, 1499, 1452, 1418, 1381, 1202, 1136 and 1099 cm$^{-1}$; EIMS (m/z): 798(M$^+$, 2), 756(2), 755(4), 707(1), 496(1), 495(5), 459(1), 458(2), 303(1), 242(1), 241(80, 231(1), 214(1), 213(3), 205 (1), 198(1), 189(1), 188(10), 187(1), 186(10), 170(4), 169(2), 168 (2), 155(1), 154(6), 140(2), 138(3), 128(4), 114(1), 113(3), 112(2), 110(1), 102(26) and 101(100%).

EXAMPLE VII

Dov-ile-Dil-Dap-Met-OMe (14)

Coupling of the dipeptide tfa salt (13) with the tripeptide tfa salt (9) following the General Procedure G which gave after purification on a silica gel column with acetone-hexane (3:2) as the eluent the required pentapeptide as a colorless thick liquid (14, 86%); R$_f$ 0.55 (acetone-hexane 3:2); [α]$_D^{25}$–45° (c 0.06, CHCl$_3$); IR(thin film): 3314, 3300, 2967, 2934, 1744, 1640, 1628, 1545, 1441, 1414, 1381, 1277, 1202, 1167, 1098, 1038 and 984 cm$^{-1}$; EIMS (m/z): 757(M$^+$, 1), 715(2), 714(6), 496(1), 495(5), 417(1), 241(4), 213(1), 186(4), 170(2), 154(2), 138(1), 128(2), 127(2), 102(10) and 101(100%).

EXAMPLE VIII-a

Dov-Val-Dil-Dap Pentyl ester (16a)

Coupling of the Dap Pentyl ester tfa salt (10a) with the tripeptide tfa salt (15) following the General Procedure G and purification using chromatography on a silica gel column with hexane-acetone (3:2) as eluent gave the required tetrapeptide ester as a colorless thick liquid (16a, 30%); R$_f$ 0.39 (hexane-acetone 3:2); [α]$_D^{25}$–69.1° (c 0.23, CHCl$_3$); IR(thin film): 3312, 3295, 2961, 2934, 2876, 1728, 1640, 1452, 1412, 1389, 1262, 1200, 1169, 1132, 1098 and 1038 cm$^{-1}$; EIMS (m/z): 668(M$^+$, 1), 625(2), 482(3), 227(3), 154(2), 128(2), 102(9) and 101(100%).

EXAMPLE VIII-b

Dov-Val-Dil-Dap Octyl ester (16b)

Coupling of the Dap Pentyl ester tfa salt (10b) with the tripeptide tfa salt (15) following the General Procedure G and purification using chromatography on a silica gel column with hexane-acetone (1:1) as eluent gave the required tetrapeptide ester as a colorless thick liquid (16b, 99%); R$_f$ 0.23 (hexane-acetone 3:1); [α]$_D^{25}$–51.3° (c 0.08, CHCl$_3$); IR(thin film): 3295, 2961, 2932, 2876, 2834, 1730, 1643, 1622, 1526, 1454, 1416, 1385, 1343, 1304, 1262, 1200, 1173, 1134, 1099, 1038 and 721 cm$^{-1}$; EIMS (m/z): 710(M$^+$, 0.7), 667(2), 481(3), 227(4), 199(1), 186 (4), 184(0.9), 155(1), 154(2), 128(2), 117(1), 102(10) and 101(100%).

EXAMPLE VIII-c

Dov-Val-Dil-Dap hexylamide (16c)

Coupling of the Dap-Hexylamide tfa salt (10c) with the tripeptide tfa salt (15) following the General Procedure G and purification using chromatography on a silica gel column with hexane-acetone (3:2) as eluent gave the required tetrapeptide amide as a colorless thick liquid (16c, 65%); R$_f$ 0.23 (hexane-acetone 3:2); [α]$_D^{25}$–48.8° (c 0.5, CHCl$_3$); IR(thin film): 3308, 3295, 2961, 2930, 2876, 1620, 1545, 1535, 1452, 1416, 1383, 1200, 1167, 1134 and 1099 cm$^{-1}$; EIMS (m/z): 681(M$^+$), 666, 650, 638, 525, 481, 449, 412, 355, 341, 269, 253, 227, 214, 199, 186, 170, 154, 128, 114, 102 and 101(100%).

From the foregoing, it is readily apparent that a useful embodiment of the present invention has been herein described and illustrated which fulfills all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

Accordingly, what is claimed is:

1. A composition of matter having the general structure appearing below:

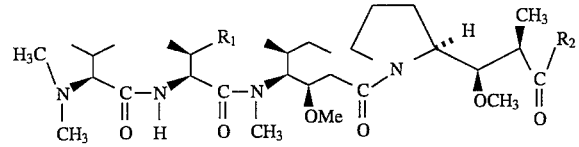

in which R$_1$ and R$_2$ are selected from the substituents as shown below:

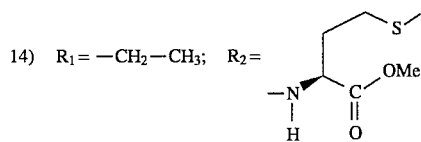

| | | |
|---|---|---|
| R$_1$=CH$_3$; R$_2$=—O—CH$_2$CH$_2$CH$_2$CH$_2$CH$_3$ | | 16a) |
| R$_1$=CH$_3$; R$_2$=—O—CH$_2$CH$_2$CH$_2$CH$_2$CH$_2$ CH$_2$CH$_2$CH$_3$ | | 16b) |
| R$_1$=CH$_3$; R$_2$=—NH—CH$_2$CH$_2$CH$_2$CH$_2$CH$_2$CH$_3$. | | 16c) |

2. A composition of matter according to claim 1 in which

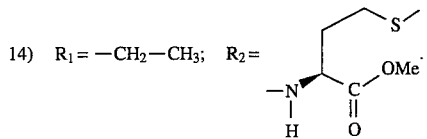

3. A composition of matter according to claim 1 in which R$_1$=CH$_3$; R$_2$=—O—CH$_2$CH$_2$CH$_2$CH$_2$CH$_3$.

4. A composition of matter according to claim 1 in which R$_1$=CH$_3$; R$_2$=—O—CH$_2$CH$_2$CH$_2$CH$_2$CH$_2$CH$_2$CH$_2$CH$_3$.

5. A composition of matter according to claim 1 in which R$_1$=CH$_3$; R$_2$=—NH—CH$_2$CH$_2$CH$_2$CH$_2$CH$_2$CH$_3$.

* * * * *